US008864745B2

(12) United States Patent
Ciavarella et al.

(10) Patent No.: US 8,864,745 B2
(45) Date of Patent: Oct. 21, 2014

(54) SACRIFICIAL CATHETER

(71) Applicant: C. R. Bard, Inc., Murray Hill, NJ (US)

(72) Inventors: David J. Ciavarella, Short Hills, NJ (US); Eddie K. Burnside, Bountiful, UT (US); Kelly B. Powers, North Salt Lake, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 32 days.

(21) Appl. No.: 13/646,483

(22) Filed: Oct. 5, 2012

(65) Prior Publication Data

US 2013/0030413 A1    Jan. 31, 2013

Related U.S. Application Data

(62) Division of application No. 13/016,881, filed on Jan. 28, 2011, now Pat. No. 8,764,728.

(60) Provisional application No. 61/299,722, filed on Jan. 29, 2010.

(51) Int. Cl.
*A61M 25/098* (2006.01)
*A61M 25/01* (2006.01)
*A61B 5/107* (2006.01)
*A61B 5/042* (2006.01)

(52) U.S. Cl.
CPC .......... *A61B 5/0422* (2013.01); *A61M 25/0102* (2013.01); *A61B 5/1076* (2013.01)
USPC .. 604/529; 600/424; 604/164.01; 604/164.11

(58) Field of Classification Search
USPC .................. 604/117, 164.01, 164.05, 164.11, 604/164.13, 165.01, 165.02, 165.04, 528, 604/529, 165.03; 600/372–374, 380, 381, 600/393, 585, 424–428; 606/41–50; 607/116, 119, 122, 124, 125, 133–138
See application file for complete search history.

(56) References Cited

U.S. PATENT DOCUMENTS 4,319,580 A    3/1982  Colley et al.
4,552,127 A *  11/1985 Schiff .............................. 600/18
(Continued)

FOREIGN PATENT DOCUMENTS

CN      102821676 A    12/2012
EP       2528497 A1    12/2012
WO    2011094631 A1     8/2011

OTHER PUBLICATIONS

PCT/US2011/023050 filed Jan. 28, 2011 International Preliminary Report on Patentability dated Aug. 9, 2012.

(Continued)

*Primary Examiner* — Kami A Bosworth
(74) *Attorney, Agent, or Firm* — Rutan & Tucker, LLP

(57) ABSTRACT

A sacrificial catheter assembly and method of use for placing a functional catheter within the body of a patient, such as into the patient's vasculature, is disclosed. In one embodiment, the sacrificial catheter assembly comprises a sacrificial catheter including an elongate body that defines a longitudinally extending lumen. A stylet is removably received within the lumen of the sacrificial catheter such that the catheter and stylet can be advanced together to a target destination within the body of the patient. The sacrificial catheter is configured so as to then be proximally slid over the stylet to remove the sacrificial catheter from the body while the stylet remains in place at the target destination. A functional catheter can then be distally slid over the stylet to place the functional catheter at the target destination. The stylet can then be removed from the body of the patient.

20 Claims, 6 Drawing Sheets

(56) References Cited

U.S. PATENT DOCUMENTS

| | | | |
|---|---|---|---|
| 5,098,388 A * | 3/1992 | Kulkashi et al. | 604/158 |
| 5,385,146 A * | 1/1995 | Goldreyer | 600/374 |
| 6,259,938 B1 | 7/2001 | Zarychta et al. | |
| 7,316,667 B2 | 1/2008 | Lindstrom et al. | |
| 8,137,317 B2 * | 3/2012 | Osypka | 604/164.05 |
| 2002/0040232 A1 | 4/2002 | Divino, Jr. et al. | |
| 2006/0235355 A1 * | 10/2006 | Freas et al. | 604/164.05 |
| 2006/0270962 A1 * | 11/2006 | McGuckin et al. | 604/6.16 |
| 2007/0005053 A1 | 1/2007 | Dando | |
| 2008/0103456 A1 | 5/2008 | Johnson et al. | |
| 2008/0255475 A1 * | 10/2008 | Kondrosky et al. | 600/585 |
| 2009/0005675 A1 * | 1/2009 | Grunwald et al. | 600/424 |
| 2009/0234328 A1 | 9/2009 | Cox et al. | |
| 2009/0259124 A1 | 10/2009 | Rothenberg | |
| 2010/0036227 A1 | 2/2010 | Cox et al. | |
| 2010/0222664 A1 | 9/2010 | Lemon et al. | |
| 2011/0015533 A1 | 1/2011 | Cox et al. | |
| 2011/0098561 A1 | 4/2011 | Thornton et al. | |
| 2011/0125107 A1 * | 5/2011 | Slocum et al. | 604/272 |
| 2011/0190712 A1 | 8/2011 | Ciavarella et al. | |

OTHER PUBLICATIONS

PCT/US2011/023050 filed Jan. 28, 2011 International Search Report dated Apr. 20, 2011.

PCT/US2011/023050 filed Jan. 28, 2011 Written Opinion dated Apr. 20, 2011.

U.S. Appl. No. 13/016,881, filed Jan. 28, 2011 Non-Final Office Action dated Dec. 6, 2012.

U.S. Appl. No. 13/016,881, filed Jan. 28, 2011 Non-Final Office Action dated May 14, 2013.

* cited by examiner

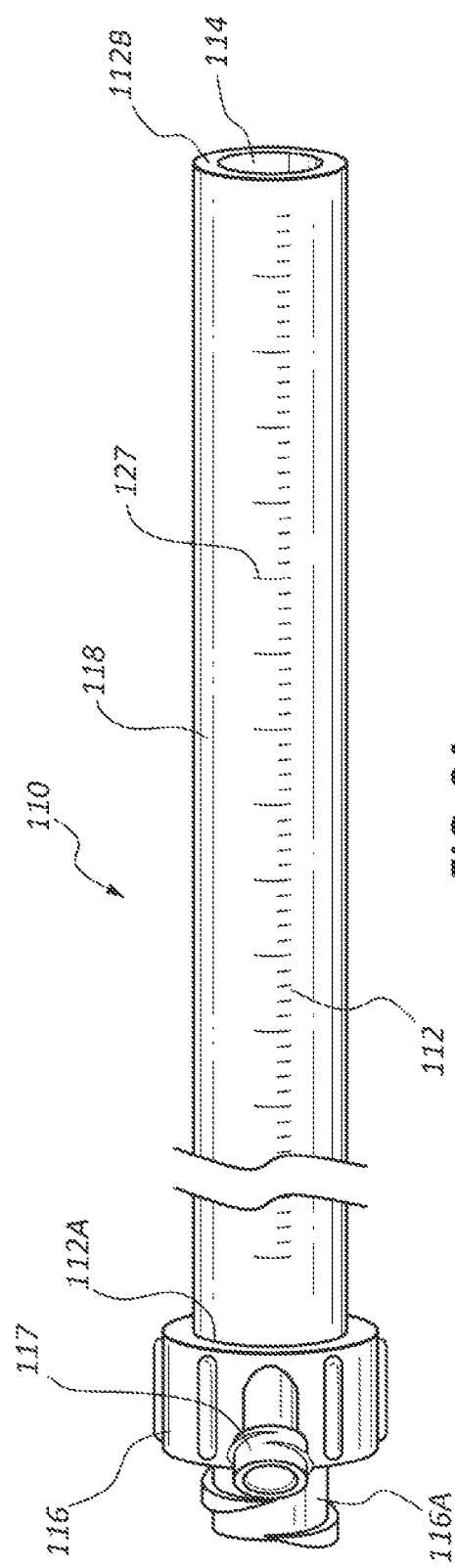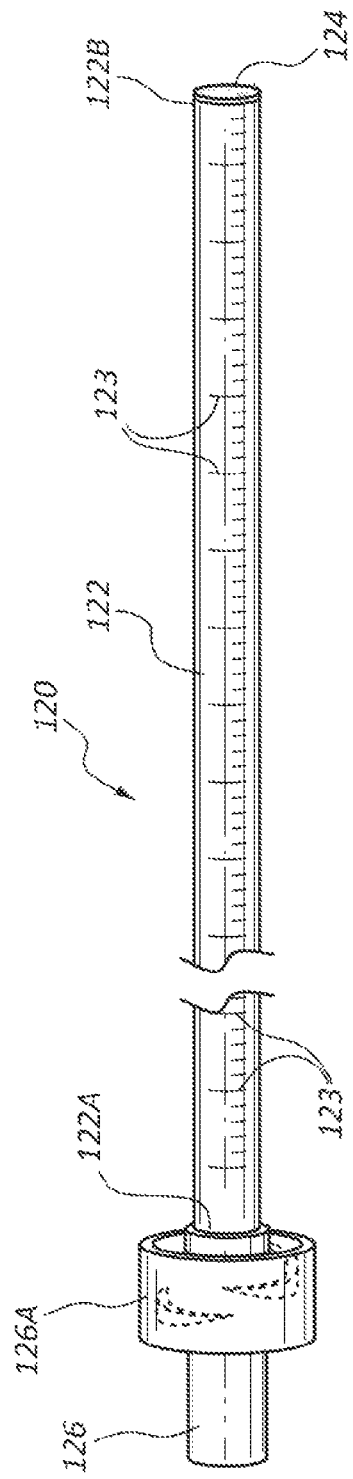
FIG. 2A
FIG. 2B

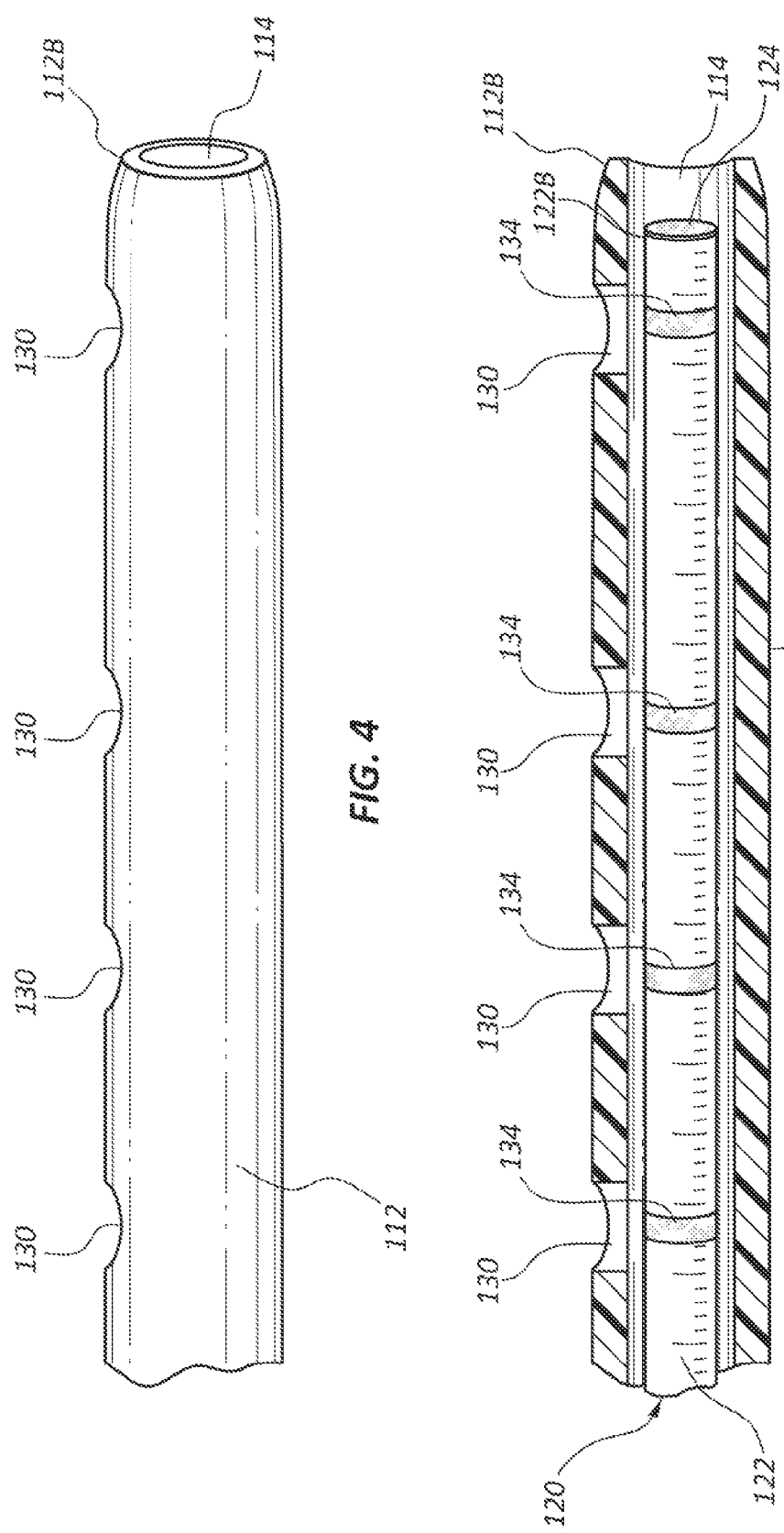

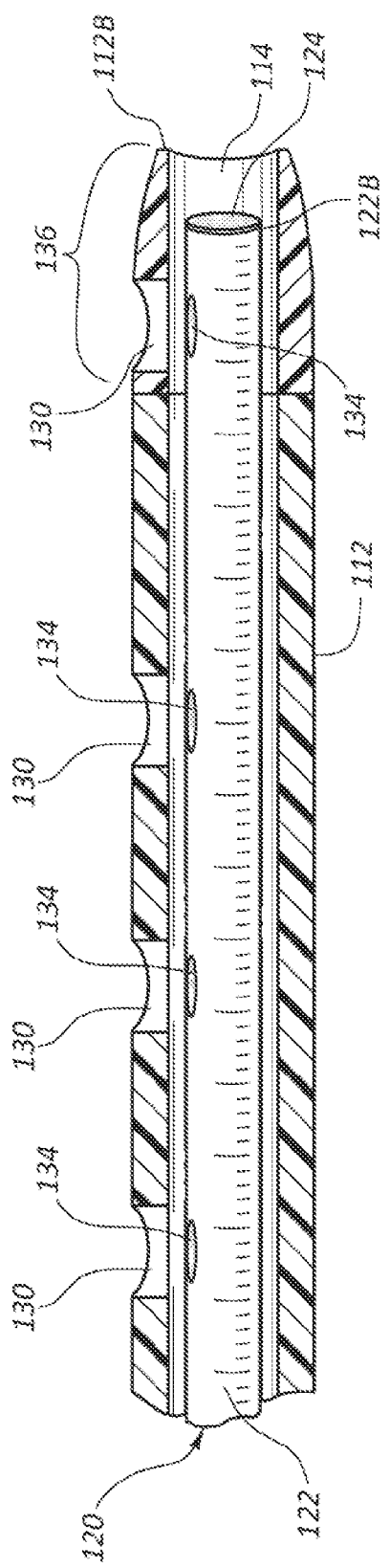
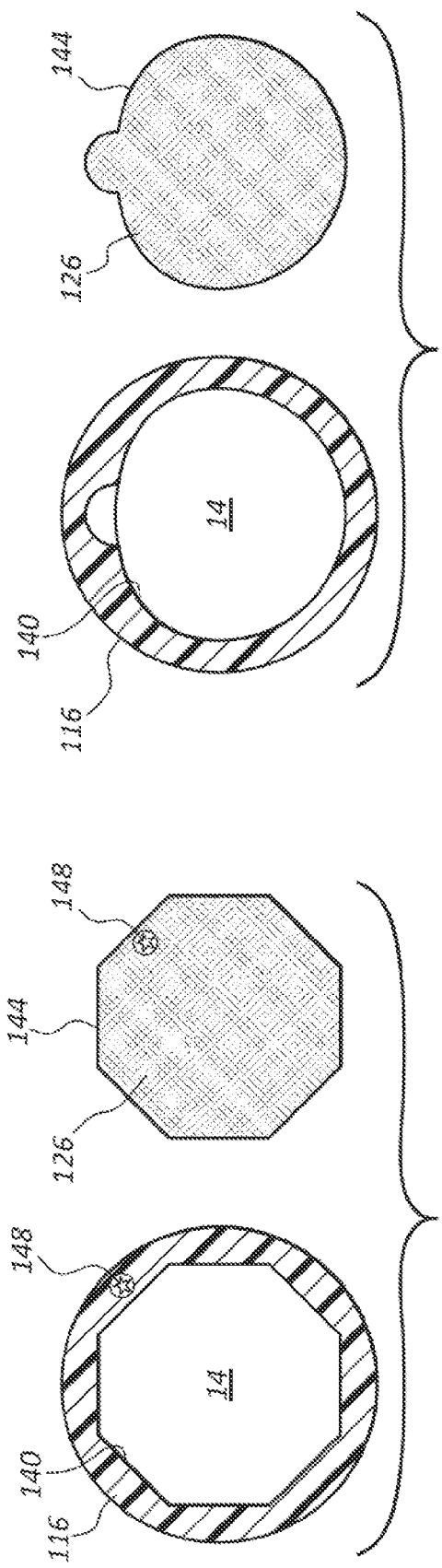

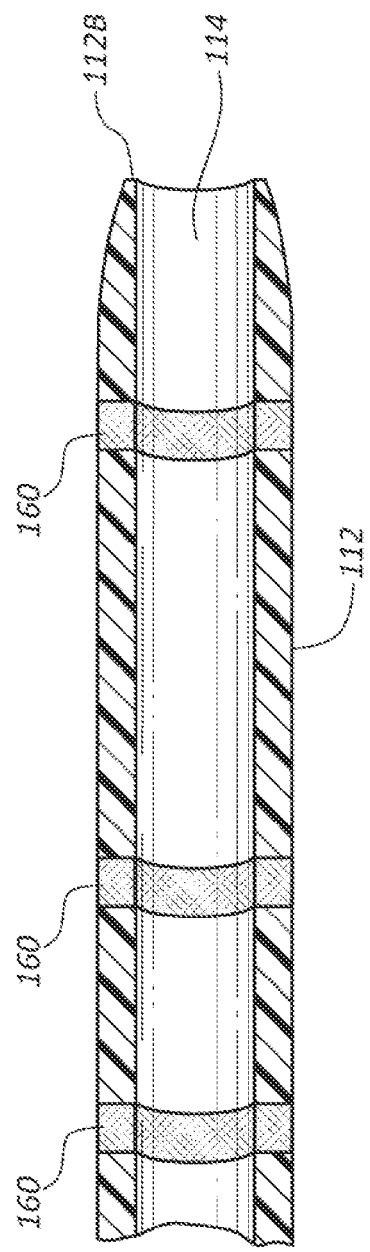

SACRIFICIAL CATHETER

CROSS-REFERENCE TO RELATED APPLICATIONS

This application is a division of U.S. patent application Ser. No. 13/016,881, filed Jan. 28, 2011, now U.S. Pat. No. 8,764,728, which claims the benefit of priority to U.S. Provisional Application No. 61/299,722, filed Jan. 29, 2010, each of which is incorporated herein by reference in its entirety into this application.

BRIEF SUMMARY

Briefly summarized, embodiments of the present invention are directed to a sacrificial catheter assembly and method of use for placing a functional catheter within the body of a patient, such as into the patient's vasculature. In one embodiment, the sacrificial catheter assembly comprises a sacrificial catheter including an elongate body that defines a longitudinally extending lumen. A stylet is removably received within the lumen of the sacrificial catheter such that the catheter and stylet can be advanced together to a target destination within the body of the patient. The sacrificial catheter is configured so as to be proximally slid over the stylet to remove the sacrificial catheter from the body while the stylet remains in place at the target destination. A functional catheter can then be distally slid over the stylet to place the functional catheter at the target destination. The stylet can then be removed from the body of the patient.

As will be seen, the sacrificial catheter and stylet cooperate to facilitate stylet-assisted placement of a functional catheter under a relatively broader range of catheter placement scenarios than would otherwise be possible. In addition, in one embodiment the stylet can include electrodes to enable the sacrificial catheter assembly to cooperate with an ECG monitoring system to advance the sacrificial catheter and stylet to the target destination via ECG-based guidance.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 2A is a side view of a sacrificial catheter in accordance with one embodiment;

FIG. 2B is a side view of a stylet for use with the sacrificial catheter of FIG. 2A, in accordance with one embodiment;

FIG. 4 is a side view of a sacrificial catheter including a plurality of side holes in accordance with one embodiment;

FIG. 5 is a partial cross sectional side view of the catheter of FIG. 4 with a stylet including band electrodes disposed therein in accordance with one embodiment;

FIG. 6 is a partial cross sectional side view of the catheter of FIG. 4 with a stylet including point electrodes disposed thereon in accordance with one embodiment;

FIG. 7 shows end views of a sacrificial catheter and stylet including one example of clocking features to facilitate mutual alignment therebetween;

FIG. 8 shows end views of a sacrificial catheter and stylet including another example of clocking features to facilitate mutual alignment therebetween; and FIG. 9 is a cross sectional side view of a sacrificial catheter including conductive bands for sensing an ECG signal according to one embodiment.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

Embodiments of the present invention are generally directed to a sacrificial catheter assembly and method of use for placing a functional catheter within the body of a patient, including the placement of a catheter into the patient's vasculature, for instance. In one embodiment, the sacrificial catheter assembly includes a sacrificial catheter with a preloaded stylet removably disposed within a lumen thereof. As will be seen, the sacrificial catheter and stylet cooperate to facilitate stylet-assisted placement of a functional catheter under a relatively broader range of catheter placement scenarios than would otherwise be possible.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Further, the words "including," "has," and "having," as used herein, including the claims, shall have the same meaning as the word "comprising."

Figure 1:
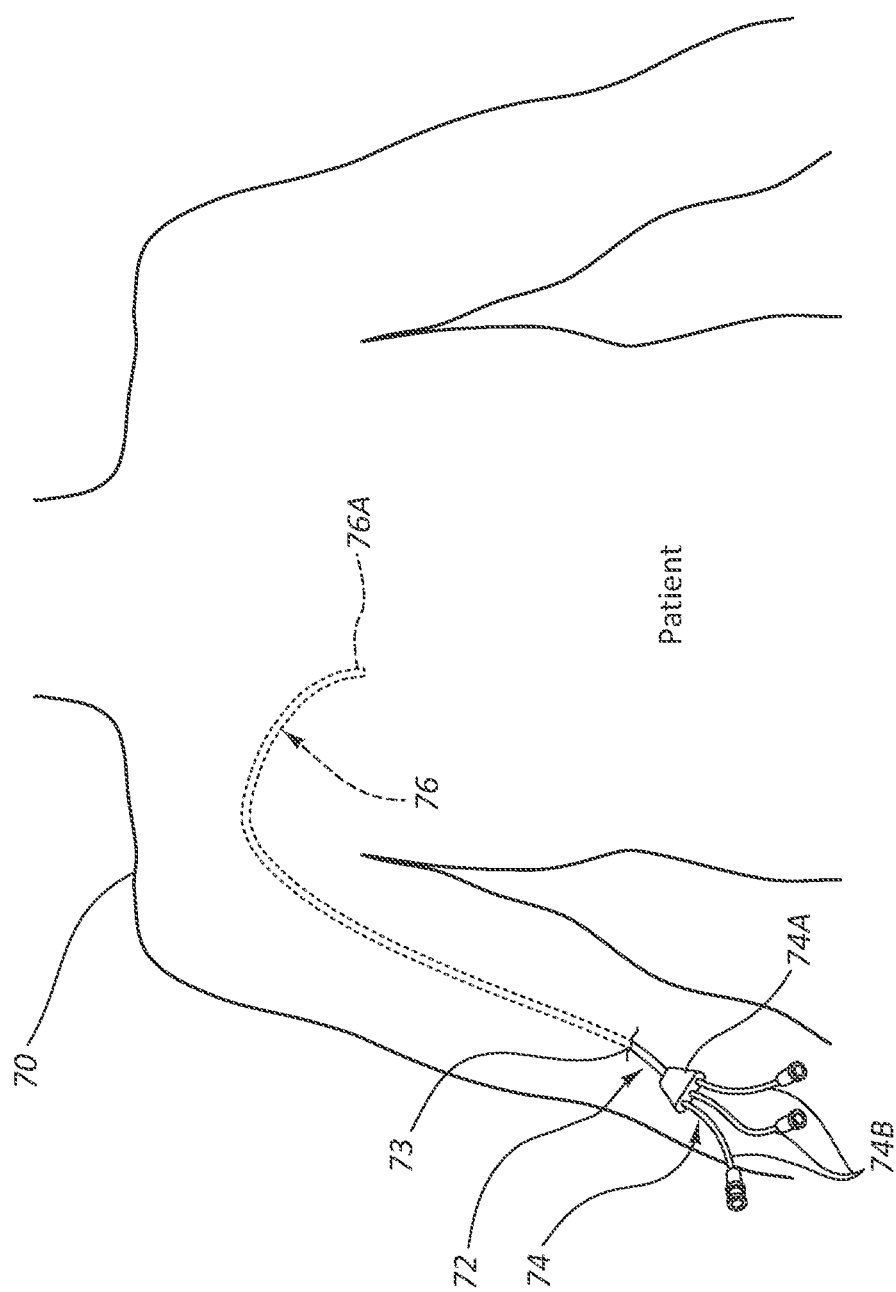
FIG. 1 is a simplified view of a patient and a catheter being inserted therein as one example of an environment where an embodiment of the present invention can be practiced.

Reference is first made to FIG. 1, which depicts one example environment wherein the sacrificial catheter assembly described herein may be employed. In particular, FIG. 1 depicts various details regarding the placement of a functional catheter 72 within the vasculature of a patient 70 through a skin insertion site 73. The functional catheter 72 generally includes a proximal portion 74 that remains exterior to the patient and a distal portion 76 that resides within the patient vasculature after placement is complete. Specifically, FIG. 1 shows that a distal tip 76A of the functional catheter 72 is positioned at a desired position, or target destination, within the patient vasculature. In one embodiment, the target destination for the catheter distal tip 76A is proximate the patient's heart, such as in the lower one-third ($\frac{1}{3}^{rd}$) portion of the Superior Vena Cava ("SVC"). Of course, the catheter distal tip can be placed in a variety of other locations.

The functional catheter proximal portion 74 further includes a bifurcation 74A that provides fluid communication between the one or more lumens of the functional catheter 72 and one or more extension legs 74B extending proximally from the bifurcation. As will be seen, the sacrificial catheter assembly to be described herein can be employed to facilitate placement of the functional catheter 72 within the patient vasculature as depicted in FIG. 1, or in other intra-corporeal locations as one skilled in the art will understand.

Reference is now made to FIGS. 2A and 2B, which depict elements of a sacrificial catheter assembly, generally designated at 110 and configured in accordance with one example embodiment of the present invention. As shown, the sacrificial catheter assembly 110 includes an elongate sacrificial catheter 112 including a body defining an open proximal end 112A, an open distal end 112B, and a lumen 114 extending therebetween.

The sacrificial catheter 112 can define one of a variety of French sizes and cross sectional shapes while still benefiting from the principles described herein. The sacrificial catheter 112 can be formed from one or more of a variety of materials, including polyurethane, polyvinyl chloride, and/or silicone, for instance.

A handle 116 for assisting with handling of the sacrificial catheter is attached to the proximal end 112A of the sacrificial catheter 112 and defines a passage therein that cooperates with the lumen 114 of the catheter. A side port 117 or other suitable inlet is included with the handle 116 to enable the catheter lumen 114 to be flushed when needed. In addition, the handle 116 includes a threaded connector 116A for lockably engaging a corresponding stylet lock ring, as will be described. Note that the connector 116A can be configured in a variety of other suitable ways to enable interconnection of the sacrificial catheter with the stylet described further below.

The sacrificial catheter body 112 is configured for temporary insertion into the vasculature or other suitable internal location of a patient by a clinician. In the present embodiment, a hydrophilic coating 118 is included on both the exterior surface of the sacrificial catheter 112 and on the interior surface defining the lumen 114. The hydrophilic coating 118 facilitates ease of removal of the sacrificial catheter 112 from the patient body when its presence is no longer needed, as will be described. In another embodiment, a hydrophilic coating can be applied to an exterior surface of the stylet body 122 as well.

Figure 3:
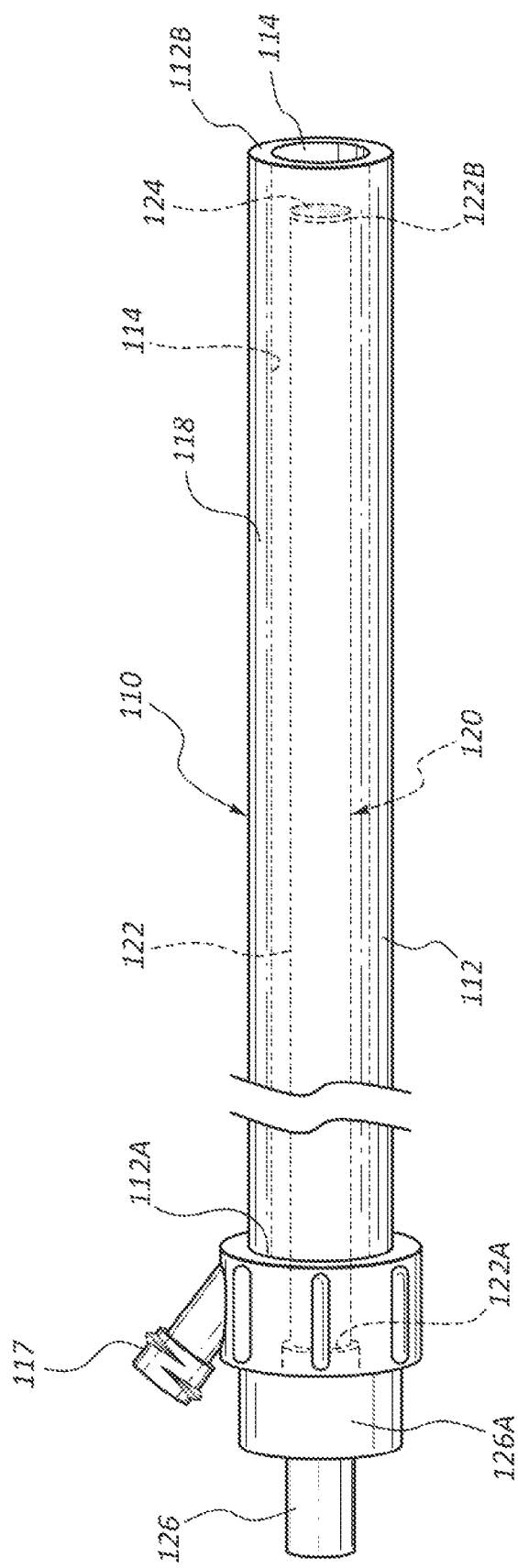
FIG. 3 is a view of the sacrificial catheter of FIG. 2A with the stylet of FIG. 2B disposed therein.

FIG. 2B shows that the sacrificial catheter assembly 110 further includes a stylet 120 that is employed, together with the sacrificial catheter 112, for assisting with the placement of a functional catheter, such as the catheter 72 shown in FIG. 1, in a desired target location within the patient vasculature, as will be seen. In particular, the stylet 120 includes an elongate body 122 that defines a proximal end 122A and a distal end 122B. In the present embodiment the stylet 120 is configured to be disposed within the lumen 114 of the sacrificial catheter 112, as shown in FIG. 3, such that the distal end 122B terminates proximate the distal end 112B of the sacrificial catheter 112. In other embodiments, the length of the sacrificial catheter is less than that of the stylet such that a distal portion of the stylet extends beyond the distal end of the sacrificial catheter when both are in place within the vasculature.

Note that, though the embodiments discussed herein describe use of a stylet, in other embodiments a guidewire or other catheter guiding apparatus could be employed. As such, "stylet" is intended to include other suitable, elongate guiding and/or stiffening apparatus, in accordance with the principles of the embodiments described herein.

The stylet body 122 can be formed of stainless steel, a memory material such as a nickel and titanium-containing alloy commonly known by the acronym "nitinol," and/or other suitable materials. The stylet 120 further includes a handle 126 that is attached at the proximal end 122A of the stylet body 122 to assist with handling the stylet during use of the catheter assembly 110. Note that the handle 126 is sized so as to enable the sacrificial catheter 112 to slide over the stylet 120 and handle when removal of the sacrificial catheter from the stylet is necessary, as will be discussed further below. The stylet handle 126 can further include a separate lock ring 126A that releasably locks with the connector 116A of the sacrificial catheter 112 so as to mate the proximal ends of the stylet 120 and catheter together. Note that the catheter connector 116A and stylet lock ring 126 are but one example for releasably mating the proximal ends of the sacrificial catheter 112 and stylet 120 and that many other configurations can be employed. In another embodiment, the sacrificial catheter handle 116, the stylet handle 126, or both can be omitted from the assembly.

The stylet body 122 further includes a plurality of depth markings 123 to assist in placing a functional catheter using the sacrificial catheter assembly, as will be described. The depth markings 123 can include alphanumeric identifiers, ticks, or other suitable indicia (including inch, cm, or mm gradations) to inform a clinician as to the depth of insertion of the stylet 120 within the body of the patient. Similarly, and as seen in FIG. 2A, the sacrificial catheter 112 in one embodiment can also include thereon depth markings 127 in inch, cm, mm, or other suitable gradations. The catheter depth markings 127 can correspond in longitudinal alignment with the depth markings 123 of the stylet 120 so as to assist with determining the depth of insertion of the functional catheter. In one embodiment, the depth markings 127 of the sacrificial catheter 112 can be correlated with the depth of one or more sensors disposed on the stylet 120 or on the body of the sacrificial catheter 112 itself, as discussed further below.

In the present embodiment an ECG sensor, such as an electrode 124, is included with the stylet 120, as best seen in FIG. 2B. As shown, the electrode 124 is positioned at the distal end 122B of the stylet body 122 for use with an external ECG monitoring system to determine proximity of the stylet distal tip relative to an electrical impulse-emitting node of the patient's heart, such as the SA node in one example. Such electrical impulses produced by the patient's heart are also referred to herein as "ECG signals." As will be seen, inclusion of the electrode 124 as an ECG sensor on the stylet enables the stylet to be precisely guided, while disposed within the lumen 114 of the sacrificial catheter 112, through the patient vasculature to a desired location proximate the patient's heart with the assistance of the ECG monitoring system. One example of an ECG monitoring system can be found in U.S. Patent Application Publication No. 2010/0036227, filed Sep. 10, 2009, and entitled "Apparatus and Display Methods Relating to Intravascular Placement of a Catheter." Another example of an ECG monitoring system can be found in U.S. Patent Application Publication No. 2009/0259124, filed Apr. 21, 2009, and entitled "Method of Locating the Tip of a Central Venous Catheter." Each of the foregoing applications is incorporated herein by reference in its entirety. Note that in other embodiments, no electrode need be included on the stylet if ECG-assisted placement is not needed/desired. In yet another embodiment, the electrode(s) can be located on the sacrificial catheter itself.

A conductive pathway is established between the electrode 124 and the proximal end of the stylet handle/connector 126 to enable the transfer of ECG signals detected by the electrode 124 along the length of the stylet 120. The conductive pathway in one embodiment is a conductive wire, ribbon, strand, etc. that is electrically connected to the electrode 124 and extends to the handle/connector 126. In another embodiment, the conductive pathway can be the stylet body itself. The handle 126 of the stylet 120 is configured in the present embodiment as a connector to electrically connect with the external ECG monitoring system to enable ECG signals transferred from the electrode 124 via the conductive pathway to be received by the monitoring system. For instance, a tether from the ECG monitoring system can include an alligator clip that removably attaches to the stylet handle 126 so as to permit the transfer of ECG signals from the stylet 120 to the ECG monitoring system.

It should be noted that the stylet and electrode as depicted herein are merely one example of a stylet/electrode configuration. Non-limiting examples of other stylet configurations can be found in U.S. Patent Application Publication No. 2010/0222664, filed Aug. 21, 2009, and entitled "Catheter Assembly Including ECG Sensor and Magnetic Assemblies," incorporated herein by reference in its entirety, and in the patent application publications referenced further above.

FIGS. 4 and 5 depict details of another embodiment of the sacrificial catheter assembly, wherein the distal portion of the sacrificial catheter 112 defines a plurality of holes 130 through the catheter wall that are each in communication with the lumen 114. So configured, the sacrificial catheter 112 can operably receive the stylet 120, as shown in FIG. 5. Note that the distal end of the sacrificial catheter 112 in the present embodiment is tapered to provide for atraumatic insertion into the patient vasculature.

In greater detail, FIG. 5 shows a cross sectional view of the sacrificial catheter 112 with the stylet 120 disposed therein. The stylet body 122 in the present embodiment includes the distal electrode 124 at the distal end 122B thereof, but also includes a plurality of additional electrodes 134 that are positioned in a spaced apart configuration along the length of the distal portion of the stylet body.

As with the distal electrode 124, each electrode 134 is configured to detect an ECG signal from the SA node or other ECG emitting portion of the patient heart when the sacrificial catheter 112 and preloaded stylet 120 are disposed within the patient vasculature. As such, conductive pathways for each electrode 134 are included with the stylet 120 and extend to the stylet handle/connector 126, as before, to enable the stylet to operably connect with an external ECG monitoring system. Note that the electrodes 134 can be spaced or grouped in one of a number of ways on the stylet body. Further note that in one embodiment the distal end electrode 124 can be omitted from the stylet 120, leaving only the spaced-apart electrodes 134. The number, size, type, and placement of the electrodes can vary according to need or application.

As best seen in FIG. 5, the holes 130 of the sacrificial catheter 112 are arranged so as to longitudinally align with the additional electrodes 134 of the stylet body 122 when the stylet 120 is properly disposed within the catheter lumen 114. The electrodes 134 in the present embodiment are configured as band electrodes, each extending circumferentially about the stylet body 122. In other embodiments, other electrode configurations can be employed. Note that non-limiting examples of other multi-electrode stylet configurations can be found in U.S. Patent Application Publication No. 2010/0222664 (referenced above) and U.S. Patent Application No. 2011/0015533, filed Sep. 29, 2010, and entitled "Stylets for use with Apparatus for Intravascular Placement of a Catheter," each of which is incorporated herein by reference in its entirety.

The sacrificial catheter assembly 110 is useful for placement of a functional catheter, such as the catheter 72 shown in FIG. 1, in situations where prior advancement of a stylet or guidewire alone, or simultaneous advancement of the stylet disposed within the functional catheter, is not possible. In such situations, the sacrificial catheter 112 containing the stylet 120 preloaded therein can be employed.

The procedure below gives further details regarding functional catheter placement using the sacrificial catheter assembly 110, according to one embodiment. Though explained using the sacrificial catheter assembly shown in FIGS. 4 and 5, the procedure can be applied to other embodiments described and contemplated herein.

Before placement of the sacrificial catheter 112 into the patient vasculature using standard catheter introduction methods, the stylet 120 is preloaded into the lumen 114 of the sacrificial catheter so as to assume the configuration shown in FIG. 5. If desired, the stylet 120 can be mated to the sacrificial catheter 112 at the proximal ends thereof by the separate stylet lock ring 126A, or by any other suitable manner. The preloaded sacrificial catheter 112 is then introduced into the patient vasculature and is advanced toward the patient's heart. As the sacrificial catheter 112 is advanced, each of the electrodes 124 and 134 of the stylet 120 begins to detect the electrical impulses produced by the SA node or other suitable node of the patient's heart, with the ECG signal detected by each electrode varying as a function of distance from the SA node. Note that the sacrificial catheter lumen 114 can be flushed with saline or other suitable liquid to ensure a conductive connection between the blood in the vasculature and the electrodes within the catheter lumen 114 via the catheter holes 130. Note further that, in one embodiment, the electrodes 124 and 136 work in concert with a reference and/or ground ECG electrode placed on the skin surface of the patient. In another embodiment, no such surface electrodes are used.

Monitoring via the ECG monitoring system of the ECG signals sensed by each of the various electrodes 124 and 136 enables a clinician to observe and analyze changes in the signal as the sacrificial catheter 112 advances toward the SA node. When the received ECG signals match a desired profile, such as a maximized P-wave of the PQRS wave complex, the clinician can determine that the stylet distal end 122B has reached a desired target position in the vasculature with respect to the SA node. In one implementation, for example, this target position lies within the lower one-third ($\frac{1}{3}^{rd}$) portion of the superior vena cava ("SVC"). In this way, the electrode-equipped stylet 120 serves as an aide in confirming proper placement of the catheter distal end 112B.

Once the sacrificial catheter-covered stylet 120 has been placed as desired within the vasculature, the sacrificial catheter 112 is no longer needed and is slid proximally off the stylet 120 and removed from the body of the patient, all while keeping the stylet in place within the vasculature. In the present embodiment, the lock ring 126A is first removed from engagement with the stylet handle 126 and sacrificial catheter handle 116 to separate the stylet 120 from the catheter 112. The hydrophilic coating 118 on the exterior and interior surfaces of the sacrificial sacrificial catheter 112 facilitate ease of removal thereof without undesirably displacing the stylet 120 or producing intimal trauma to the patient. It is thus seen that the sacrificial catheter is employed to assist with ultimate placement of a functional catheter, and is not used for therapeutic infusion or aspiration of fluids. The depth markings 123 on the stylet body 122 are consulted at the insertion site or other suitable location to determine how deeply the stylet has been inserted into the vasculature and thus how far the functional catheter should be inserted.

The functional catheter 72 (FIG. 1) is then slid over the stylet 120 and inserted into the vasculature until its distal end is positioned proximate the distal end 122B of the stylet 120, which ensures proper placement of the functional catheter.

The stylet 120 can then be removed from the patient while keeping the functional catheter 72 in place. The functional catheter 72 can then be prepared as needed for use. In addition to use of the depth markings on the stylet body, other techniques for determining the depth of functional catheter insertion into the patient vasculature may also be used.

As shown in FIG. 6, in one possible embodiment, the stylet 120 includes one or more electrodes 134 that are point electrodes, instead of the band electrodes shown in FIG. 5. In this case, the handle of the sacrificial catheter, the handle of the stylet, or both can include features to radially align the stylet with the sacrificial catheter such that the stylet electrodes 134 are not only longitudinally aligned with the corresponding holes 130 of the sacrificial catheter 112, but radially aligned as well. FIG. 7 gives one example of clocking features that can be included with the sacrificial catheter 112 and stylet 120, wherein the catheter handle 116 includes a hexagonally-shaped keyed surface 140. The handle 126 of the stylet 120 includes a corresponding hexagonally-shaped keyed surface 144 that engages with the keyed surface of the catheter handle 116 when the stylet 120 mates with the sacrificial catheter 112. An indicator 148 can be included with the keyed surfaces 140 and 144 to indicate a proper radial alignment between the holes 130 and the electrodes 134, such as that shown in FIG. 6. FIG. 8 gives another example of keyed surfaces 140 and 144, including a cavity and correspondingly shaped protrusion on the catheter handle 116 and stylet handle 126, respectively. In addition to these, many other keyed surface and clocking feature configurations for aligning the sacrificial catheter and stylet can be employed.

In another embodiment, the handles of the sacrificial catheter and stylet can be configured, such as interconnected with one another, so as to enable torqueing of the catheter assembly, which in turn enables the assembly to be steered during advancement within the patient vasculature. This interconnection can include suitable structure to withstand a longitudinal load thereon without separating or displacing the handles with respect to one another. Such structure can include, for example, a lock ring, collet, and/or compressed o-ring.

FIG. 9 depicts another embodiment of the sacrificial catheter 112, wherein the body thereof includes one or more electrically conductive bands 160 defined through the catheter wall thickness so as to pass ECG signals therethrough. Such bands 160 can be operably linked with correspondingly placed electrodes on the stylet body 122 or in other suitable ways so as to enable the detection of ECG signals when the sacrificial catheter 112 is disposed within the patient vasculature. Note that the number, shape, size, and usage of the conductive bands 160 can vary from what is described herein.

Note that in one embodiment the stylet of the sacrificial catheter assembly can include one or more magnetic elements to enable the catheter assembly to be used with a catheter placement system that employs magnetic-based stylet tip tracking in addition to ECG-based tip navigation/position confirmation technology to accurately place the catheter in the vasculature of the patient. The magnetic elements can include permanent magnets, electromagnets, or other magnetic apparatus. Further details regarding magnetic-based catheter tracking can be found in U.S. Patent Application Publication No. 2010/0036227, referenced above.

In one embodiment, the sacrificial catheter assembly can be employed in placing multi-lumen catheters, such as that shown at 72 in FIG. 1, including catheters with staggered or split distal tips. Indeed, the multi-electrode stylet of the assembly can enable the distal tips of such functional catheters to be placed in respective desired locations once the stylet has been placed and the sacrificial catheter removed. Further, it should be appreciated that in one embodiment the stylet can be re-inserted into the functional catheter at any time subsequent to initial placement to re-verify that the distal tip of the functional catheter is still positioned in a desired location within the vasculature. The depth markings on the stylet assist with such a determination.

One skilled in the art will appreciate that the sacrificial catheter assembly can be employed in medical applications beyond what is explicitly described herein, including coronary and arterial catheterizations, for instance. Moreover, it is appreciated that instead of ECG sensing electrodes, the stylet used with the sacrificial catheter can employ other technologies, such as visual camera or Doppler technologies, for example.

In yet another embodiment, the distal end of the sacrificial catheter can be configured to facilitate atraumatic insertion thereof. FIG. 6 gives one example of this, wherein a distal segment 136 of the sacrificial catheter 112 includes a relatively soft durometer material and is tapered to a relatively thin wall proximate the distal end thereof.

In one embodiment, it is appreciated that the sacrificial catheter can be used to place a guidewire, conductive wire, stylet, or other elongate wire into the vasculature of the patient, after which the sacrificial catheter is removed to leave the wire in place for use by a clinician for heart monitoring, etc. In this case, no additional component, such as a functional catheter, is placed into the vasculature.

In another embodiment, the length of the catheter can vary from the length of the stylet. For instance, the sacrificial catheter in one embodiment can be shorter than the stylet. In one implementation, for example, the catheter can be about 40 cm long while the stylet is about 135 cm long. In such a case, the distal end of the stylet would be positioned at the target destination, while the distal end of the sacrificial catheter would not, as the distal ends of the stylet and sacrificial catheter would not be co-terminal. Of course, a variety of other possible sacrificial catheter and stylet length configurations can be used.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A sacrificial catheter assembly for use in placing a functional catheter within a body of a patient, comprising:
   a sacrificial catheter including an elongate body defining a lumen extending from a proximal end to a distal end of the body; and
   a stylet removably received within the lumen of the sacrificial catheter such that the catheter and stylet can be advanced together to a target destination within the body of the patient,
   wherein the sacrificial catheter can be proximally slid over a proximal end of the stylet without compromise to the sacrificial catheter to remove the sacrificial catheter from the body while the stylet remains in place at the target destination, and wherein a functional catheter can then be distally slid over the stylet to place the functional catheter at the target destination, and wherein the stylet can then be removed from the body of the patient.

2. The sacrificial catheter assembly as defined in claim 1, wherein the stylet is torqueable so as to enable guidance of the sacrificial catheter during advancement thereof within the patient body.

3. The sacrificial catheter assembly as defined in claim 1, wherein a handle of the sacrificial catheter is releasably lockable with a handle of the stylet to enable simultaneous advancement of the stylet with the sacrificial catheter.

4. The sacrificial catheter assembly as defined in claim 3, wherein the stylet includes a plurality of depth markings thereon, and wherein a port is included with the handle of the sacrificial catheter to enable flushing of the lumen of the sacrificial catheter.

5. The sacrificial catheter assembly as defined in claim 3, wherein the stylet handle is sized to enable the sacrificial catheter to slide over the stylet and handle during removal.

6. The sacrificial catheter assembly as defined in claim 5, further comprising a separate lock ring separate from the sacrificial catheter and stylet, the separate lock ring releasably lockable to the sacrificial catheter to mate a proximal end of the stylet to a proximal end of the sacrificial catheter.

7. The sacrificial catheter as defined in claim 1, wherein a hydrophilic coating is included on at least an inner lumen surface of the catheter body.

8. The sacrificial catheter as defined in claim 1, further comprising:
    at least one hole defined through a wall of the body of the sacrificial catheter; and
    at least one ECG-sensing electrode disposed on the stylet that substantially longitudinally aligns with the at least one hole of the sacrificial catheter body when the stylet is received within the lumen of the sacrificial catheter.

9. The sacrificial catheter assembly as defined in claim 8, wherein the at least one electrode of the stylet is electrically connected to a handle of the stylet such that the handle can be operably connected to an ECG monitoring system.

10. The sacrificial catheter assembly as defined in claim 8, wherein a handle of the sacrificial catheter includes a first clocking feature and wherein a handle of the stylet includes a second clocking feature that cooperatively engages with the first clocking feature when the handles are mated so as to radially align the at least one electrode of the stylet with the at least one hole of the sacrificial catheter body.

11. The sacrificial catheter assembly as defined in claim 10, wherein the first and second clocking features define inter-engaging keyed surfaces for mating the handles of the sacrificial catheter and the stylet.

12. The sacrificial catheter as defined in claim 8, wherein the at least one electrode of the stylet includes a first electrode disposed at a distal end of the stylet and a plurality of additional electrodes disposed along a length of a distal portion of the stylet.

13. The sacrificial catheter assembly as defined in claim 12, wherein the at least one electrode and the additional electrodes include at least one of a point electrode and a band electrode.

14. The sacrificial catheter as defined in claim 1, wherein a distal segment of the sacrificial catheter includes a soft durometer material and is tapered to reduce a wall thickness of the distal segment, and wherein the body of the sacrificial catheter includes at least one conductive band defined through a thickness of a wall of the sacrificial catheter.

15. The sacrificial catheter as defined in claim 1, wherein a length of the sacrificial catheter body is shorter relative to a length of the stylet such that a distal portion of the stylet extends beyond a distal tip of the sacrificial catheter.

16. The sacrificial catheter as defined in claim 1, wherein the sacrificial catheter further includes at least one conductive band defined through a wall of the elongate body for sensing an ECG signal of the patient.

17. The sacrificial catheter assembly as defined in claim 1, further comprising a releasable lock such that a proximal end of the stylet is mated to a proximal end of the sacrificial catheter in a locked configuration and slidably coupled in an unlocked configuration, wherein the releasable lock permits the sacrificial catheter to slide over the proximal end of the stylet in the unlocked configuration.

18. A sacrificial catheter assembly, comprising:
    a sacrificial catheter including an elongate body defining a lumen, the body defining a plurality of side holes in fluid communication with the lumen; and
    a stylet for removable insertion within the lumen of the sacrificial catheter, the stylet including a plurality of electrodes for sensing an ECG signal, wherein at least one of the electrodes is longitudinally aligned with a corresponding one of the side holes of the sacrificial catheter when the stylet is received within the lumen,
    wherein the sacrificial catheter is removable from the stylet after placement of the sacrificial catheter and stylet at a target destination within a vasculature of a patient so as to enable placement of a functional catheter within the vasculature over the stylet to position a distal end of the functional catheter at the target destination within the vasculature.

19. The sacrificial catheter assembly as defined in claim 18, wherein the electrodes are also radially aligned with the corresponding side holes of the sacrificial catheter.

20. The sacrificial catheter assembly as defined in claim 18, wherein the body of the sacrificial catheter includes a plurality of depth markings thereon, wherein the body of the stylet includes a plurality of depth markings thereon, and the depth markings of the sacrificial catheter and the stylet are correlated with one another.

* * * * *